United States Patent [19]

Malabarba et al.

[11] Patent Number: 5,674,840
[45] Date of Patent: Oct. 7, 1997

US005674840A

[54] SYNTHETIC AGLUCODALBAHEPTIDE ANTIBIOTICS

[75] Inventors: Adriano Malabarba, Binasco; Romeo Ciabatti, Novate Milanese, both of Italy

[73] Assignee: Gruppo Lepetit SpA, Gerenzano, Italy

[21] Appl. No.: 532,629

[22] PCT Filed: Apr. 14, 1994

[86] PCT No.: PCT/EP94/01154

§ 371 Date: Dec. 26, 1995

§ 102(e) Date: Dec. 26, 1995

[87] PCT Pub. No.: WO94/26780

PCT Pub. Date: Nov. 24, 1994

[30] Foreign Application Priority Data

May 19, 1993 [GB] United Kingdom ............. 93108139

[51] Int. Cl.$^6$ ..................................................... A61K 38/00
[52] U.S. Cl. ................................. 514/9; 514/11; 530/317
[58] Field of Search ............................ 530/317; 514/9, 514/11

[56] References Cited

U.S. PATENT DOCUMENTS 5,438,117  8/1995  Malabarba et al. .................. 530/317

OTHER PUBLICATIONS

Malabarba et al., *J. Antibiotics*, 42, (1989), 1684–1697.
Malabarba et al., *J. Med. Chem.*, Oct. 30, 1992, 35(22), 4054–60.

*Primary Examiner*—Cecilia J. Tsang
*Assistant Examiner*—C. Delacroix-Muirhead
*Attorney, Agent, or Firm*—Ruth E. Homan

[57] ABSTRACT

Synthetic aglucodalbaheptides of formula (I) wherein W and Z, each independently, represent the relative portions of the aglycon of an antibiotic of the dalbaheptide group. Y represents a carboxylic group or a functional derivative of said carboxylic group; R and $R_1$, each independently, represent hydrogen or a protecting group of the amino function. $R_2$ represents hydrogen; and their salts with acid and bases as well as their inner salts. A process for producing the aglucodabaheptides of formula (I) and their use as medicaments.

13 Claims, No Drawings

5,674,840

SYNTHETIC AGLUCODALBAHEPTIDE ANTIBIOTICS

This invention concerns synthetic aglucodalbaheptides of general formula (I)

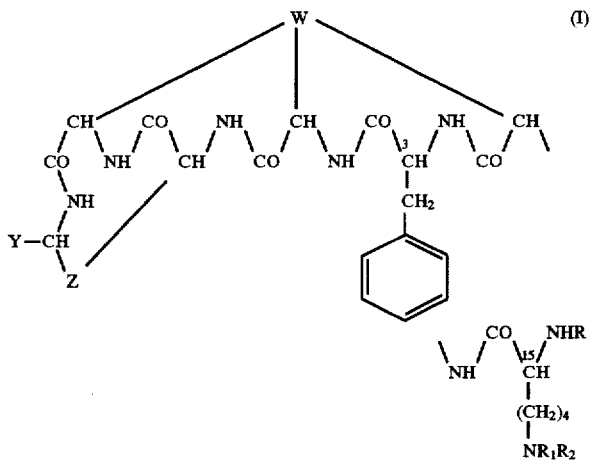

wherein:

W and Z, each independently, represent the relative portions of the aglycon of an antibiotic of the dalbaheptide group (aglucodalbaheptides);

Y represents a carboxylic group or a functional derivative of said carboxylic group;

R and $R_1$, each independently, represent hydrogen or a protecting group of the amino function.

$R_2$ represents hydrogen.

The invention includes the salts of the above represented synthetic aglucodalbaheptides with acids or bases as well as their inner salts.

A further object of this invention is a process for producing the aglucodalbaheptide antibiotics of formula (I) above starting from the tetrapeptides of formula (II)

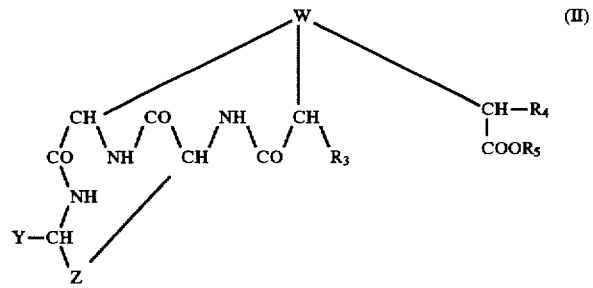

wherein:

W and Z, each independently, represent the relative portions of the aglycon of an antibiotic of the dalbaheptide group (aglucodalbaheptides);

Y represents a carboxylic group or a functional derivative of said carboxylic group;

$R_3$ and $R_4$, each independently, represent amino or a protected amino group; and $R_5$ is hydrogen or a protecting group of the carboxylic function.

The tetrapeptides of general formula (II) above, their salts and their method of manufacture are described in International Application Publication No. WO92/10517. The above mentioned International Application contains also an exhauxtive description of the naturally occurring dalbaheptide antibiotics and their classification in four sub-groups referred respectively as ristocetin-type, vancomycin-type, avoparcin-type and synmonicin-type dalbaheptides.

The pentapeptide precursors suitable for the preparation of the above mentioned tetrapeptides are described in European Patent Application Publication No. 409 045.

With the term dalbaheptides are usually defined all antibiotic substances having in common a highly modified linear heptapeptidic structure made up of seven amino acids, five of which are constantly aryl- and arylmethyl-amino acids, said structure being determinant of a common mechanism of action, i.e. the specific complexation with the D-alanyl-D-alanine terminus of one or more intermediates of the cell wall synthesis which leads to cell disruption (see also: F. Parenti and B. Cavalleri, "Novel glycopeptide antibiotics of the dalbaheptide group", Drugs of the future, Vol. 15 (1): 57–72, (1990) and B. Cavalleri, F. Parenti: "Glycopeptides (dalbaheptides)", in Kirk-Othmer's Encyclopedia of Chemical Technology, Vol. 2, 995–1018, J. Wiley & Sons, 1992).

According to a preferred embodiment of this invention the synthetic aglucodalbaheptides of the formula (I) above comprise those derivatives wherein:

W=

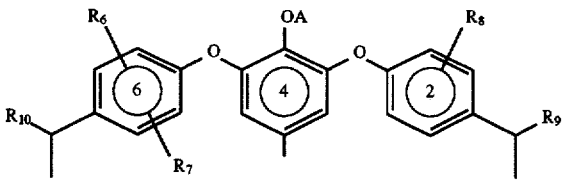

Z=

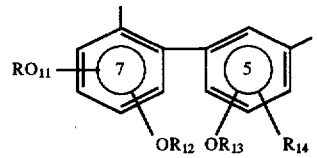

wherein:

i): A is hydrogen or a protecting group of the phenolic hydroxy moiety; $R_6$, $R_7$ and $R_8$ are, each independently, hydrogen or halogen wherein the halogen preferably is chloro or bromo and, most preferably, are in the ortho position with respect to the ether bond; $R_9$ and $R_{10}$ are, each independently, hydrogen or a group $OR_{15}$ wherein $R_{15}$ is hydrogen or a protecting group of the benzylic hydroxy moiety.

As shown in formula (I) above, the group W is simultaneously linked to the second, fourth and sixth amino acid (starting from the right) moiety of the heptapeptidic chain of the aglucodalbaheptides;

ii): the groups $OR_{11}$ and $OR_{12}$, preferably, are in, respectively, the para and ortho position with respect to the bond connecting the two phenyl rings and the radical $R_{11}$ and $R_{12}$, each independently, represent hydrogen or a protecting group of the phenolic hydroxy moiety; the group $OR_{13}$, preferably, is in the position ortho with respect to the bond connecting the two phenyl rings and the radical $R_{13}$ represents hydrogen or a protecting group of the phenolic hydroxy moiety; the group $R_{14}$, preferably, is in the position meta with respect to the bond connecting the two phenyl rings and represents hydrogen or halogen, preferably, hydrogen or chloro.

As represented in formula (I) above, the group Z is linked to the amino acids corresponding to the fifth and seventh amino acid (starting from the right) moieties of the heptapeptidic chain of the aglucodalbaheptides.

The encircled numbers in the aromatic rings indicate the respective amino acids of the aglucodalbaheptide chain to which the specific aryl or aralkyl moiety is bound.

The symbol Y in formula (I), represents a carboxylic group, a functional derivative thereof, preferably, an ester. Such ester derivatives include the protected carboxylic groups from which the free carboxylic group can be easily restored under specific conditions which do not affect the amino acid chain. This definition includes the lower alkyl esters derivatives as well as the esters formed by reaction of the carboxylic function with aliphatic alcohols bearing substituents (e.g. hydroxy, halo, lower alkoxy, amino, lower alkylamino, di-(lower alkyl)amino, cyano and phenyl, optionally substituted by lower alkyl, lower alkoxy, halo or nitro) in the aliphatic chain.

The term "functional derivative of the carboxylic group" includes also the carboxamides moieties which are described in International Application Publication No. WO92/10517 where the meanings of the symbol Y of the tetrapeptide starting material of formula (II) are illustrated in more details. Said carboxamide moieties are functional derivatives resulting from the reaction of the carboxylic group with aliphatic, cicloalyphatic and heterocyclic amines. In particular, among the aliphatic amines, the lower alkylamines and the di-lower alkylamines are preferred and may optionally contain a substituent on the aliphatic chain such as amino, lower alkylamino, di-(lower alkyl)amino, pyrrolidino, piperazino, N-(lower alkyl)piperazino, morpholino, hydroxy, lower alkoxy, carboxy, carbo(lower alkoxy), carbamyl, mono- and di-(lower alkyl)carbamyl and the like; among the cycloaliphatic amines, the $C_4$–$C_7$ cycloaliphatic primary amines are preferred; among the heterocyclic amines, saturated nitrogen containing 5 to 7 membered heterocyclic ring moieties are preferred, e.g. pyrrolidine, morpholine, piperazine, and N-(lower alkyl) piperazine.

The salts of the end compounds of formula (I), and of starting compounds of formula (II) are those deriving from the salification with an acid of the basic functions of the molecule, e.g., the amino moieties NHR and/or $NR_1R_2$.

Representative acid addition salts are those formed by reaction with both inorganic and organic acids, for example, hydrochloric, sulfuric, phosphoric, succinic, citric, lactic, maleic, fumaric, cholic, d-glutamic, d-camphoric, glutaric, phthalic, tartaric, methanesulfonic, benzenesulfonic, benzoic, salicylic, trifluoroacetic acid and the like. Alternatively, the salts may be formed through salification of the carboxylic acid function represented by the symbol Y with an appropriate base, such as, for instance, an alkali metal hydroxide or carbonate or an organic amine, such as a mono-, di- or tri-(lower alkyl)amine, a mono-, di- or tri-(hydroxy-lower alkyl)amine.

The inner salts of the aglucodalbaheptides of formula (I) are those formed through internal salification in the cases of simultaneous presence of basic (e.g. amino) and acid (e.g. carboxylic) functions of sufficient strength in the same compound.

In the formula (I) above and in the other related formulas in this description and claims the chiral center of each of the five basic aryl-and arylmethyl-amino acids of the aglucodalbaheptides has the same absolute configuration as that of the respective amino acid of the natural dalbapeptide from which the tetrapeptide starting material (II) has been obtained.

The chiral centers which are synthetically introduced into the aglucodalbaheptides of this invention and are indicated with the index 3 and 15, respectively, in the formula (I) above, may have both R and S absolute configuration, depending on the absolute configuration of the amino acid which is inserted.

However, according to a preferred embodiment of this invention, the configuration of the introduced chiral center identified with the index 3 is S, while the configuration of the chiral center identified with the index 15 may be both R and S, most preferably, R.

A most preferred group of aglucodalbaheptide antibiotics according to this invention comprises those derivatives of formula (Ia)

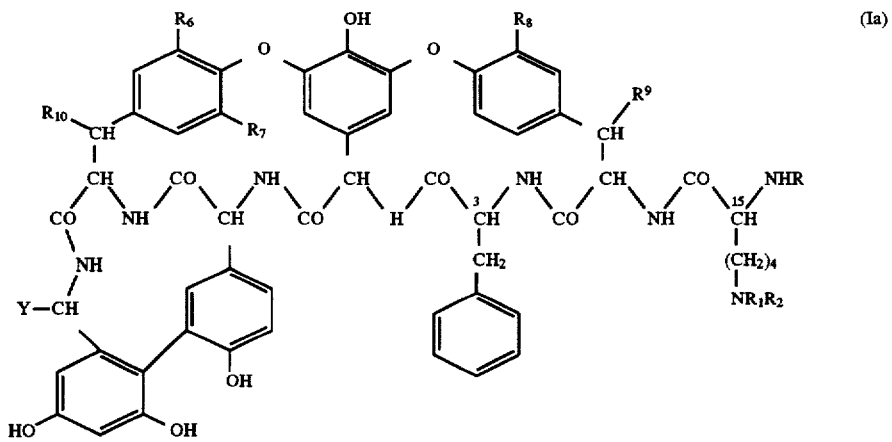

wherein:

Y represents a carboxylic group or a lower alkyl ester derivative of said carboxylic group;

R and $R_1$, each independently, represent hydrogen or a protecting group of the amino function, preferably, hydrogen;

$R_2$ represents hydrogen;

$R_6$ represents hydrogen;

$R_7$ and $R_8$ each independently represent hydrogen or chloro;

$R_9$ represents hydrogen or hydroxy, preferably hydrogen;

$R_{10}$ represents hydrogen or hydroxy; and their salts with acids and bases, preferably, their salts with the pharmaceutically acceptable acids and bases, as well as their inner salts.
According to this invention the process for the manufacture of the aglucodalbaheptide antibiotics of formula (I) is running through the following Reaction Scheme 1.
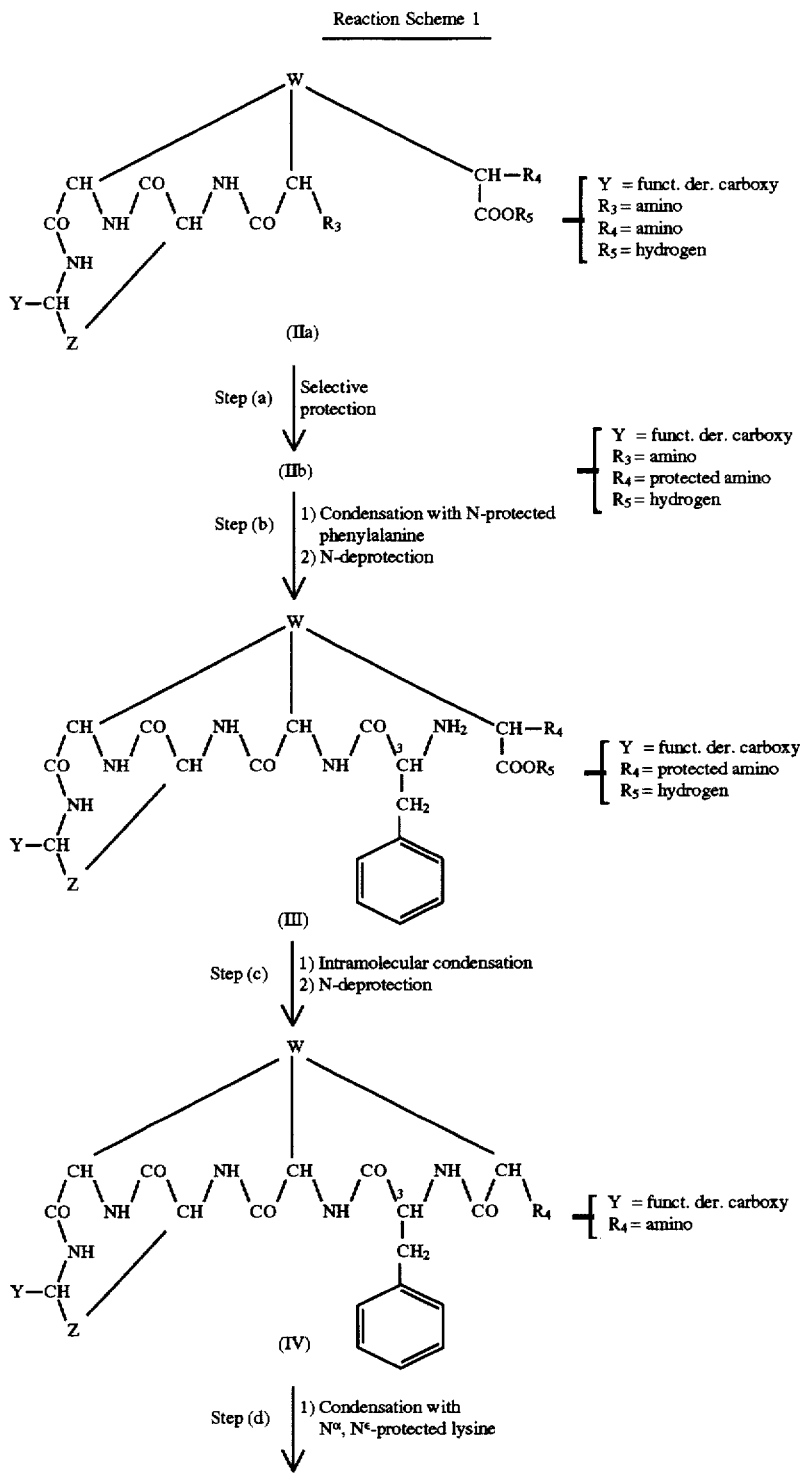

-continued
Reaction Scheme 1

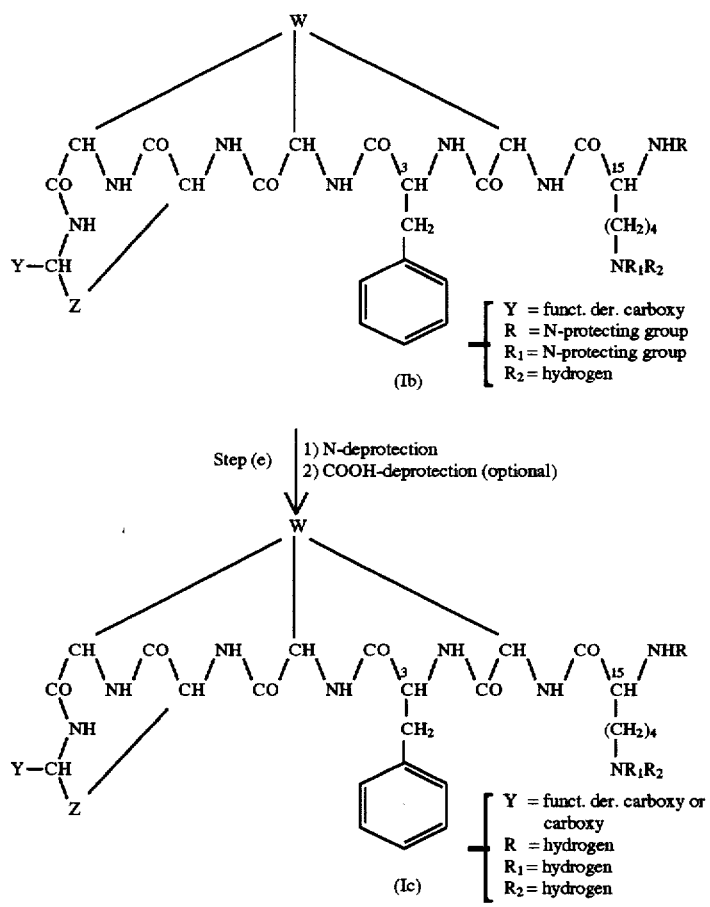

(Ib)
Y = funct. der. carboxy
R = N-protecting group
R₁ = N-protecting group
R₂ = hydrogen Step (e) 1) N-deprotection
2) COOH-deprotection (optional)

(Ic)
Y = funct. der. carboxy or carboxy
R = hydrogen
R₁ = hydrogen
R₂ = hydrogen In the above Reaction Scheme the symbols W and Z have the same meanings as above, while the term "funct. der. carboxy" relative to the meaning of the symbol Y means that such symbol represents a functional derivative of the carboxylic group as described before, including a protected carboxylic group which can be deprotected at the end of the process.

The first Step (a) of the above reaction scheme involves the selective protection of the amino group represented by the symbol $R_4$ in the tetrapeptide (TP) of formula (IIa) to yield the TP of formula (IIb).

Said selective protection may be accomplished, for instance, by protecting first the more reactive amino group identified with the symbol $R_3$ in the TP of formula (IIa), then, protecting the amino group represented by the symbol $R_4$ with a different type of protecting group which is not cleaved under the conditions required for the subsequent elimination of the protection (deprotection) of the amino group identified with the symbol $R_3$.

This last operation leads to a TP compound (IIb) wherein $R_4$ is a protected amino group and $R_3$ is a free amino group apt to react with the selected amino acid derivative, that is, N-protected phenylalanine, to form a pentapeptide (PP) according to reaction Step (b). This step is completed by the elimination of the N-protecting group originating from the N-protected phenylalanine precursor, thus yielding the PP of formula (III).

The performance of the above described reaction Step (b), involves the application of reaction conditions where the presence of a free carboxy group in the position Y would negatively affect the reaction course. Therefore, it is preferred to use a TP derivative (IIb) wherein Y represents a functional derivative of said carboxylic group to avoid any undesired interference of the free carboxylic group when the condensation conditions are applied for the coupling of the N-protected phenylalanine with the TP (IIb) to form the PP (III).

For analogous reasons, it is preferred to maintain the protection of the carboxy group represented by the symbol Y also in the successive steps involving the formations of other peptidic bonds.

In the performance of the above mentioned reaction steps as well as in the successive reactions it is not necessary to provide protection to the phenolic or benzylic hydroxy groups which may be contained in the portion W and Z of the TP and PP. However, if these protecting groups are originally present in the TP of formula (II), as obtained according to International Application Publication No. WO92/10517, they may be maintained during all the successive reaction course and may be optionally cleaved at the end of the whole process, when the aglucodalbaheptide (Ib) or (Ic) is obtained.

The successive Step (c) involves an intramolecular condensation between the free amino group of the PP (III) and the carboxylic moiety $COOR_5$ wherein $R_5$ is hydrogen. Also in this case the reaction course would be negatively affected by the presence of an additional free carboxylic group in the position Y of the PP. In fact, such additional carboxylic group would take part to intermolecular coupling reactions with the free amino group yielding undesired side-products. Therefore, in this case it is particularly important to maintain the protection of such carboxylic group as described above. The Step (c) includes also the N-deprotection of the amino group represented by the symbol $R_4$ to form the intermediate hexapeptide (HP) of formula (IV).

The following Step (d) involves the addition of the second amino acid by condensation with a $N^\alpha,N^\epsilon$-protected lysine derivative, to yield the aglucodalbaheptide derivative (Ib) which, in the successive Step (e), can be submitted to the N-deprotection of the amino groups of the lysine moiety. If desired, when Y is an easily cleavable protected carboxy group, said protected carboxy group can be de-protected to yield the aglucodalbaheptide (Ic) wherein Y is a carboxylic group.

In the following description are given more specific details on the way each Step of the above described process may be carried out.

Step (a):

The crucial point for the performance of this Step is the selection of a reagent suitable for introducing a protecting group of a primary amino function which preferentially reacts with the amino group represented by the symbol $R_3$ in formula (IIa).

With respect to this desired effect, it has been found that satisfactory selectivity and yields are obtained by employing di-tert-butyldicarbonate as the reagent furnishing the N-protecting group.

This reagent is contacted in an about equimolecular amount with the TP of formula (IIa) in a solution consisting of a mixture of water and an inert water miscible organic solvent preferably selected from lower alkanols, acetone, tetrahydrofuran, dioxane and dimethoxyethane at a temperature between $-5°$ and $20°$ C., preferably between $0°$ and $10°$ C. at a pH between 6 and 8, preferably between 6.5 and 7.5.

The proportion between water and organic solvent is varying between 1:9 and 9:1, preferably between 4:6 and 6:4.

The desired product of formula (IIa) wherein $R_3$ is a tert-butoxycarbonylamino group (all other symbols having the same meanings as indicated in the Reaction Scheme 1) is usually obtained together with some amount of a side-product of formula (IIa) wherein both $R_3$ and $R_4$ represent tert-butoxycarbonylamino moieties.

The side-product can be easily separated from the desired mono-protected product, for instance, by extraction of an acid aqueous mixture containing both products with a water immiscible solvent.

The recovered side-product can be converted to the unprotected starting material by means of acid hydrolysis (e.g. with trifluoroacetic acid). The regenerated starting material, in turn, is reacted again with di-tert-butyldicarbonate under the above described conditions. If needed, the regenerating process of the side-product material followed by reaction with di-tert-butyldicarbonate can be repeated two or three times in order to obtain a high conversion yield of the desired mono-protected product.

The mono-protected product is then submitted to a further intermediate process for protecting the free amino group represented by the symbol $R_4$ with a protecting group which is not cleaved under the acidic treatment conditions which are required to remove the tert-butoxycarbonyl group. Reagents that can be used to achieve the above desired effect may be selected from those forming carbamate derivatives.

Examples of such reagents and the relative reaction conditions are described, for instance, in the book by T. W. Greene and P. G. M. Wuts: "Protective Groups in Organic Synthesis" second edition. J. Wiley, New York, 1991 (see, in particular, pages 315–348).

Accordingly, the following protecting groups are particularly suitable for the protection of the amino group identified with the symbol $R_4$ in the TP of formula (IIb): 9-fluorenylmethoxycarbonyl, 9-(2-sulfo)fluorenylmethoxycarbonyl, 9-(2,7-di-bromo)fluorenylmethoxycarbonyl, 2,7-di-tert-butyl[9-(10,10-dioxo-thioxanthenyl)]methoxycarbonyl, 1,1-dimethyl-2,2-dibromoethoxycarbonyl, 1,1-dimethyl-2,2,2-trichloroethoxycarbonyl, allyloxycarbonyl, benzyloxycarbonyl, p-nitrobenzyloxycarbonyl, p-bromobenzyloxycarbonyl, 2,4-dichlorobenzyloxycarbonyl and 4-methylsulfinylbenzyloxycarbonyl.

According to a preferred embodiment of this invention, the benzyloxycarbonyl radical is employed as protecting group of the amino function represented by the radical $R_4$ in formula (IIa). For this purpose, the above mentioned mono-protected TP of formula (IIa) wherein $R_3$ represents a tert-butoxycarbonylamino moiety is reacted with a suitable reagent capable of introducing such benzyloxycarbonyl group on the amino function, for example, benzylchloroformate in the presence of an excess of a mild base, e.g. sodium bicarbonate, potassium bicarbonate, or a tri-(lower alkyl) amine.

The reactant providing the N-protecting group is usually employed in an equimolecular amount with respect to the TP. However, in certain cases it may be necessary to employ a slight molecular excess (up to 20 per cent) of such reagent to complete the reaction.

The reaction is usually carried out in the presence of a solvent preferably consisting of a mixture of water and a water miscible inert organic solvent, such as those described above for the introduction of the tert-butoxycarbonyl moiety. The reaction temperature is maintained between $0°$ and $50°$ C., preferably between $15°$ and $30°$ C. The di-protected TP obtained according to the above procedure is then submitted to acidic treatment suitable for the selective removal of the tert-butoxycarbonyl group.

Such treatment consists, for instance, of contacting the di-protected TP with an excess of dry trifluoroacetic acid at a temperature between $5°$ and $30°$ C. for 5 to 25 minutes.

The TP of formula (IIb) wherein $R_4$ is a benzyloxycarbonylamino moiety (all other symbols having the same meanings as in Reaction Scheme 1) is then recovered from the reaction medium according to procedures per se known in the art.

Step (b):

This step consists in reacting the N-protected TP of formula (IIb) with a suitable derivative of phenylalanine. Such derivative must be protected on the amino group and must contain an activating group of the carboxy moiety suitable for promoting the condensation process. The protecting group of the amino moiety of the phenylalanine must be different from that of the $R_4$ portion of the TP, since it must be removed in the next step under conditions which do not affect such $R_4$ portion.

A solution of this problem consists in employing a carbamate forming group which can be cleaved under the same conditions which have been applied in the former Step (a). The tert-butoxycarbonyl moiety is, therefore, one of the preferred N-protecting groups for the phenylalanine.

The activating group of the N-protected phenylalanine carboxylic function may be selected from those forming the usual activated ester moieties.

Examples of activated esters are those described in general terms as amino acid esters for peptide coupling in the book by L. F. Fieser and M. Fieser, "Reagent for organic Synthesis" J. Wiley, New York.

Activated esters forming reagents which can be used to activate the carboxy function of the N-protected phenylalanine are for instance those described by R. Schwyzer et al. in Helv. Chim. Act., 1955, 38, 69–70 and include the following:

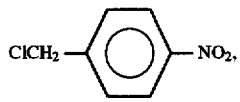

$ClCH_2CH_2N(C_2H_5)_2$

Other activating groups of the carboxylic function of the N-protected phenylalanine that can be employed according to the process of this invention are the esters of the carboxylic moiety with the following hydroxy compounds:

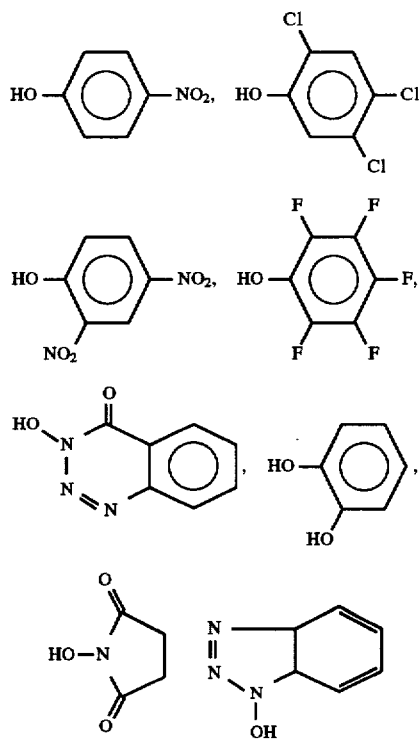

as described by J. Jones in "The Chemical Synthesis of Peptides", pages 55–58, Clarendon Press-Oxford (1991)

According to one preferred embodiment of this invention the ester of N-protected phenylalanine with N-hydroxysuccinimide is employed for the condensation reaction with the TP of formula (IIb).

The condensation reaction is carried out under the general conditions required for the formation of polypeptides. Usually, the two reactants are contacted in about equimolecular amounts (in the presence of an about equimolecular amount of an organic tertiary amine, e.g. a tri-(lower alkyl) amine,if the amino group $R_3$ in compound (IIb) is in the form of an acid addition salt) in an organic inert solvent at a temperature between 5° and 35° C., preferably between 15° and 25° C. The organic inert solvent is usually selected from organic amides, (e.g. dimethylformamide), polyethers (e.g. dimethoxyethane), cyclic ethers (e.g.tetrahydrofuran), lower aliphatic esters (e.g. etyl acetate) and dimethylsulfoxide. A preferred solvent is dimethylformamide.

The di-protected PP derivative which forms following the condensation reaction is then treated under conditions promoting the cleavage of the N-protected amino group of phenylalanine residue, without affecting the N-protected amino group $R_4$, thus yielding the PP of formula (III). In the case where the amino group of phenylalanine is protected through the formation of a tert-butylcarbamate and $R_4$ is benzyloxycarbonylamino, the preferred treatment is essentially the same as that applied at the end of Step (a) for the removal of the protecting tertbutoxycarbonyl group of the $R_3$ amino moiety of the corresponding TP.

Step (c):

The mono protected PP (III) resulting from the previous reaction is submitted to intramolecular condensation for the formation of a peptidic bond between the free amino group of the phenylalanine moiety and the carboxylic group $COOR_5$ wherein $R_5$ is hydrogen.

The intramolecular condensation apparently occurs only under well defined conditions by selecting appropriate condensing agents, solvents, reagents proportions and temperature. The intramolecular reaction occurs via activation of the carboxylic group $COOR_5$ of the PP of formula (III) by reaction with N-hydroxybenzotriazole in the presence of dicyclohexylcarbodiimide. The conditions for the formation of the activated carboxy derivative of the PP require that the carboxy group $COOR_5$ is first salified with an organic tertiary amine such as diethylamine, N-methylpyrrolidine, N-methylpiperazine or N-methylmorfoline before reacting with N-hydroxybenzotriazole. The PP, the organic amine and the N-hydroxybenzotriazole are employed in about equimolecular amounts while the dicyclohexylcarbodiimide is employed in a 10 to 20 per cent molar excess. The reaction is preferably carried out in a solvent mixture consisting of dimethylformamide and dichloromethane in about equal volumes. The temperature of the reaction mixture is kept between 10° and 35° C. for a sufficient period of time to complete the intramolecular condensation. The time required may be determined by following the reaction course with the usual analytical systems which include TLC and HPLC methods.

The solid recovered from this reaction may be purified by reverse phase column chromatography, for instance, on silica-gel by using a linear gradient of from 10 to 70 per cent of acetonitrile in water and checking the collected fraction by HPLC. The fractions containing the pure N-protected HP are combined and, after concentration, the product is precipitated by addition of a non-solvent (e.g. diethyl ether). Inorganic impurities which may be present in the precipitated product may be eliminated by adding the product to dimethylsulfoxide, filtering the suspension and lyophilizing the clear filtrate.

The N-protected HP is then transformed in the HP compound of formula (IV) by removal of the protecting group of the amino moiety identified by the radical $R_4$. Said protecting group may be eliminated by applying the appropriate methods suggested by the specific literature regarding the N-protecting groups mentioned above. When the N-protecting group of the amino function identified by the radical $R_4$ is a benzyloxycarbonyl group the removal of such protecting group is usually carried out by catalytic hydrogenation at atmospheric pressure and room temperature, in the presence of an organic solvent or a mixture of organic solvents and, preferably, an aqueous mineral acid (e.g. 1N HCl). In such case, the HP of formula (IV) is recovered from the filtered hydrogenated solution as the salt with said mineral acid.

Step (d):

The HP of formula (IV) of Step (c) is condensed with a $N^\alpha,N^\delta$-protected lysine derivative activated on the carboxylic group. For both the N-protection and the activation of the carboxylic group of the lysine the same reagents that are employed for N-protection and carboxy- activation of phenylalanine in Step (b) can be utilized. The reaction conditions and the mutual proportions of the reagents and the recovery procedure are essentially the same as in the case mentioned above.

The result of this condensation is an aglucodalbaheptide of formula (Ib) wherein each of the two amino groups of the lysine portion bears an N-protecting group.

Step (e):

This Step is primarily performed for removing the two N-protecting groups of the aglucodalbaheptide (Ib). There is no special problem for this removal. In particular, when such N-protecting groups are tert-butoxycarbonyl moieties, the removal is carried out with essentially the same treatment with trifluoroacetic acid as described for the removal of the tert-butoxycarbonyl moiety from the phenylalanine portion of the PP obtained in Step (c). The aglucodalbaheptide (Ic) may be obtained from the above treatment as a free base if the residual of the evaporated trifluoroacetic acid solution is treated with an aqueous alkali solution at a pH 8.5. The free base of the aglucodalbaheptide may be further purified by reverse phase column chromatography by using essentially the same procedure and conditions applied in Step (c) for the purification of the HP of formula (IV).

When the substituent Y of the aglucodalbaheptide (Ic) is a functional derivative of the carboxylic group which is not easily cleavable under mild conditions, such function is maintained unmodified in the final compound which, however, is still part of this invention.

An aglucodalbaheptide (Ic) having a carboxylic group as substituent Y can be transformed into an aglucodalbaheptide derivative of formula (Ic) wherein Y is a functional derivative of such carboxylic function (e.g. an ester or an amide) as described above. Methods for the preparation of such functional derivatives from the corresponding free carboxylic compound are widely described in the dalbaheptides literature. In particular, see the following patent applications: EPA Publication Nos. 216775, 340245, 370283, 376041, 351685, 460448, and International Application Publication No. WO93/0360.

In a specific representative example embodying the performance of the Reaction Scheme 1 above, the TP of formula (IIa) derived from aglucoteicoplanin has been employed as the starting material. Said TP has the following structure formula

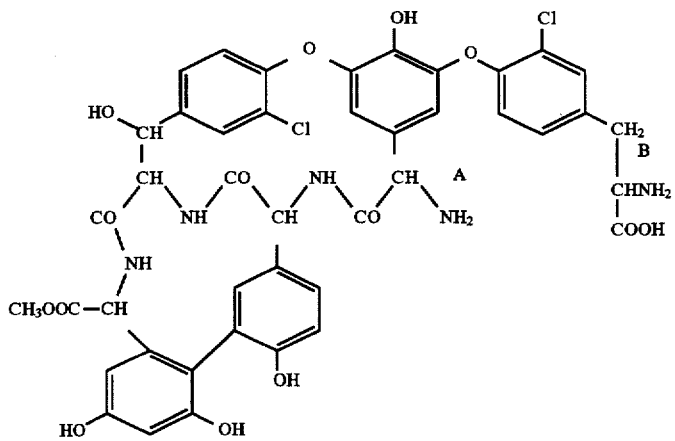

The aglucodalbaheptide of formula (Ic) wherein Y represents a protected carboxylic function, if desired, may be converted to the corresponding free carboxy derivative by removal of the protecting group.

For instance, when the protected carboxylic function is an ester with a lower alkanol, the hydrolysis of such ester may be performed by suspending the product in tetrahydrofuran and adding a molar excess (10–50%) of 1N NaOH at room temperature. The above conditions do not affect the other portions of the molecule.

and is currently indicated in the following description and examples as ATTP methyl ester. For the purpose of clarity and better understanding of the examples which follow this description, in the above formula the nitrogen atoms of the two different free amino groups have been distinguished with the letter A and B, respectively.

By following the multi-step process described above and employing the appropriately protected amino acids L-phenylalanine and D-lysine in Steps (b) and (d), respectively, the following compound falling into general formula (Ic) has been obtained

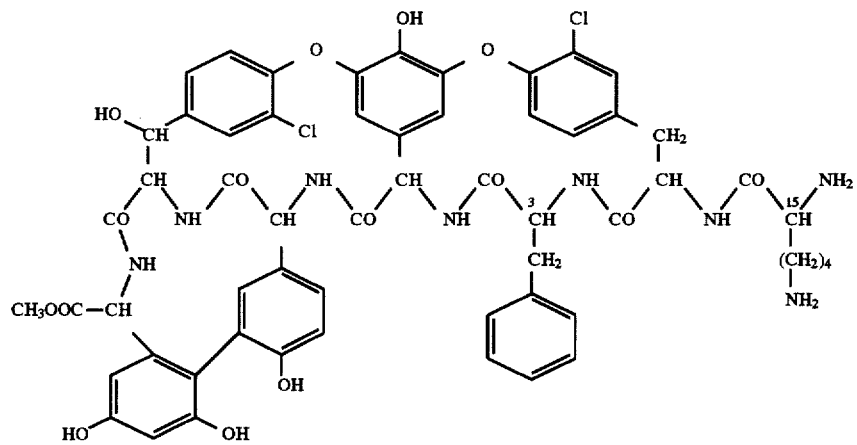

wherein the chirality centers identified with the indexes 3 and 15 have respectively S and R absolute configuration.

This reaction process runs through the preparation of the corresponding PP and HP intermediates of formula (III) and (IV) which are conventionally identified as $N^B$-protected-(L-phenylalanyl)$^3$-ATPP methyl ester and (L-phenylalanyl)$^3$-ATHP methyl ester, respectively.

The above compound has been conventionally named (L-phenylalanyl)$^3$-(D-lysyl)$^{15}$-aglucoteicoplanin dalbaheptide methyl ester [(L-phenylalanyl)$^3$-(D-lysyl)$^{15}$-ATDH methyl ester] where the apexes 3 and 15 indicate that the amino acid units containing the carbon atoms numbered as 3 and 15 in the aglucoteicoplanin basic skeleton according to A. Malabarba et al. J. Antibiotics 42, 1684–1697, (1989) are replaced by a L-phenylalanine and a D-lysine moiety, respectively. The absolute configuration of the chirality centers identified with the index 3 and 15 is S and R, respectively, as described above.

This compound shows a remarkable antimicrobial activity in in vitro experiments as reported in the following TABLE 1 wherein teicoplanin and teicoplanin aglycon are taken as the reference compounds.

TABLE 1

MIC (mg/l)

| (L No.) | Strain | (L-phenylalanyl) 3-(D-lysyl)15-aglucoteico-planin dalbaheptide methyl ester | teico-planin | teico-planin aglycon |
|---|---|---|---|---|
| (165) | Staph. aurevi Tour | 0.13 | 0.13 | 0.13 |
| (819) | s. aureus Smith | 0.13 | 0.25 | 0.06 |
| (561) | s. aureus clin. isol. | 0.06 | 8 | 0.13 |
| (147) | S. epidermidis ATCC 12,228 | 0.13 | 8 | 0.06 |
| (533) | S. epidermidis clin. isol. | 0.13 | 8 | 0.016 |
| (602) | S. haemolyticus clin. isol. | 0.5 | 32 | 0.25 |
| (49) | Strep. pyogenes C203 | 0.25 | 0.13 | 0.13 |
| (44) | Strep. pneumoniae UC41 | 0.13 | 0.13 | 0.13 |
| (149) | Enterococcus faecalis ATCC 7,080 | 0.5 | 0.13 | 0.13 |
| (502 | E. faecalis clin. isol. | 16 | >128 | >128 |

The in vitro antibacterial activity of the compounds is determined by means of standard agardilution tests in microtiter. Iso-Sensitest broth (Oxoid) is used for all bacteria except streptococci (Todd-Wewitt broth, Difco) and enterococci (Mueller-Hinton, Difco). Broth cultures are diluted so that the final inoculum was about 5×10$^5$ cfu/ml (colony forming units per ml). All broth microdilution MICs are performed in the presence of 0.01% bovine serum albumin (Pentax fraction V, Sigma). MIC (minimal inhibitory concentration) is considered as the lowest concentration which shows no visible growth after incubation at 37° C. for 18–24 hours.

The above synthetically obtained aglucodalbaheptide, while maintaining substantially the same level of activity as the teicoplanin aglycon against most of the bacteria which are usually sensitive to the dalbaheptides, is surprisingly active also against a clinical isolate of Enterococcus faecalis which is resistant to both teicoplanin and teicoplanin aglycon.

By using the process of this invention and selecting as starting materials other TP compounds which can be prepared according to International Application Publication No. W092/10517 a series of synthetic aglucodalbaheptides of formula (I) can be obtained.

Moreover, compounds of formula (I) with different configurations at C$_3$ and C$_{15}$ may be obtained by using phenylalanine and lysine starting materials having appropriate chirality. If racemic amino acid materials are employed, mixtures of diastereomers of formula (I) are obtained.

The compounds of the present invention can be employed as the active ingredients of the antimicrobial preparations used in human and veterinary medicine for the prevention and treatment of infectious diseases caused by pathogenic bacteria which are susceptible to said active ingredients, in particular, for the treatment of infections caused by, Streptococci, Staphylococci and Enterococci strains, including Enterococcus faecalis strains resistant to teicoplanin, an antibiotic currently used in the therapy of severe infectious diseases.

The compounds of the present invention can be administered orally, topically or parenterally, the parenteral administration route being preferred.

Depending on the route of administration, these compounds can be formulated into various dosage forms.

Preparations for oral administration may be in the form of capsules, tables, liquid solutions or suspensions. As known in the art, the capsules and tablets may contain in addition to the active ingredient, conventional excipients such as diluents, e.g. lactose, calcium phosphate, sorbitol and the like, lubricants, e.g. magnesium stearate, talc, polyethylene glycol, binding agents, e.g. polyvinylpyrrolidone, gelatin, sorbitol, tragacanth, acacia, flavoring agents, and acceptable disintegrating and wetting agents. The liquid preparations, generally in the form of aqueous or oily solutions or suspensions, may contain conventional additives such as suspending agents.

For topical use the compounds of the present invention may also be prepared in suitable forms for absorption through the mucous membranes of the nose and throat or bronchial tissues and may conveniently take the form of liquid sprays or inhalants, lozenges, or throat paints.

For medication of the eyes or ears, the preparation may be presented in liquid or semi-liquid form. Topical applications may be formulated in hydrophobic or hydrophilic bases as ointments, creams, lotions, paints, or powders.

For rectal administration the compounds of the invention are administered in the form of suppositories admixed with conventional vehicles, such as, for example, cocoa butter, wax, spermaceti or polyethylenglycols and their derivatives.

Compositions for injection may take such forms as suspensions, solutions, or emulsions in oily or aqueous vehicles, and may contain formulatory agents such as suspending, stabilizing and/or dispersing agents.

Alternatively, the active ingredient may be in powder form for reconstitution at the time of delivery with a suitable vehicle, such as sterile water.

The amount of active principle to be administered depends on various factors such as the size and conditions of the subject to be treated, the route and frequency of administration, and the causative agent involved.

The compounds of the invention are generally effective at a dosage comprised between about 1 and about 40 mg of active ingredient per Kg of body weight. Depending on the characteristics of the specific compound, the infection and the patients, the effective dose can be administered in a single administration per day or divided in 2 to 4 administrations per day. Particularly desirable compositions are in the prepared in the form of dosage units containing from about 30 to about 500 mg per unit.

EXAMPLE 1

Preparation of $N^B$-benzyloxycarbonyl-aglucoteicoplanin tetrapeptide methyl ester [$N^B$-CBZ-ATTP methyl ester; Reaction Scheme 1, formula (IIb)]

i) Preparation of $N^A$-tert-butoxycarbonylaglucoteicoplanin tetrapeptide methyl ester ($N^A$-t-BOC-ATTP methyl ester)

A stirred solution of 3 g (about 3 mmol) of ATTP methyl ester (the synthesis of this compound is described in International Application Publication No. WO92/10517) in 100 ml of dioxane:water 1:1 mixture is adjusted at pH 7 by adding solid NaHCO$_3$. Then, a solution of 0.65 g (about 3 mmol) of di-tert-butyldicarbonate in 20 ml of dioxane is added dropwise while cooling at 0° C. The reaction mixture is stirred at 0° C. for 18 hours, and then is poured into 400 ml of a mixture water:ethyl acetate 1:1.

After adjusting at pH 3 with 1N HCl:

a) the organic layer is separated, washed with water (3×100 ml), dried over Na$_2$SO$_4$, and then it is concentrated, at 30° C. under reduced pressure, to a small volume (about 25 ml). On adding diethyl ether (100 ml), the precipitated solid is collected, yielding 1.4 g of side-product $N^A$,$N^B$-di-(t-BOC)-ATTP methyl ester (HPLC: Method A, $t_R$ 25.2 minutes);

b) the aqueous phase is extracted with an equal volume of butanol and the butanol layer is concentrated at 40° C. under reduced pressure to a small volume (about 30 ml). On adding diethyl ether (100 ml), the precipitated solid is collected to give 1.5 g of $N^A$-t-BOC-ATTP methyl ester (TABLE 2, compound 1; HPLC: Method A, 16.4 minutes).

The above di-protected side-product $N^A$,$N^B$-di-(t-BOC)-ATTP methyl ester (1.4 g) is treated with trifluoroacetic acid (50 ml) at room temperature (10 minutes) to regenerate ATTP methyl ester (1.15 g) which is then transformed into 0.7 g of $N^A$-t-BOC-ATTP methyl ester and 0.5 g of the above side product under the same above conditions. By repeating this process three times, the overall conversion yield of ATTP methyl ester to $N^A$-t-BOC-ATTP methyl ester is about 80%.

ii) Preparation of $N^A$-tert-butoxycarbonyl-$N^B$-benzyloxycarbonyl aglucoteicoplanin tetrapeptide methyl ester ($N^A$-t-BOC-$N^B$-CBZ-ATTP methyl ester).

To a stirred solution of 2.35 g (about 2.3 mmol) of $N^A$-t-BOC-ATTP methyl ester in 100 ml of a dioxane:water 1:1 mixture, which is adjusted at pH 7 with solid NaHCO$_3$, a solution of 0.32 ml (about 2.3 mmol) of benzyl chloroformate in 10 ml of dioxane is added dropwise at room temperature in 10 minutes. The reaction mixture is stirred at room temperature for 20 minutes and then it is poured into 150 ml of water. The resulting cloudy solution is adjusted at pH 3 with 1N HCl and extracted with 200 ml of ethyl acetate. The organic layer is separated, dried over Na$_2$SO$_4$, and then it is concentrated, at 30° C. under reduced pressure, to a small volume (about 20 ml). On adding diethyl ether (100 (100 ml), the precipitated solid is collected, yielding 2.4 g of $N^A$-t-BOC-$N^B$-CBZ-ATTP methyl ether (TABLE 2, compound 2; HPLC: Method B, $t_R$ 11.8 minutes).

iii) Preparation of $N^B$-CBZ-ATTP methyl ester.

A solution of $N^A$-t-BOC-$N^B$-CBZ-ATTP methyl ester (2.4 g) in 100 ml of dry trifluoroacetic acid is stirred at room temperature for 10 minutes, and then the solvent is evaporated at 35° C. under reduced pressure. The oily residue is dissolved in 300 ml of a mixture water:ethyl acetate 1:1. The organic layer is separated, washed twice with water (2×150 ml), dried over Na$_2$SO$_4$, and then it is concentrated, at 40° C. under reduced pressure, to a small volume (about 15 ml). On adding diethyl ether (100 ml) the solid precipitate is collected to give 2 g of $N^B$-CBZ-ATTP methyl ester as trifluoroacetate (TABLE 2, compound 3, analytical data reported for the free base; HPLC: Method B, $t_R$ 8.3 minutes).

EXAMPLE 2

Preparation of $N^B$-benzyloxycarbonyl-(L-phenylalanyl)$^3$-aglucoteicoplanin pentapeptide methyl ester [$N^B$-CBZ-(L-phenyl alanyl)$^3$-ATPP methyl ester; Reaction Scheme 1, formula (III)]

i) Preparation of $N^B$-benzyloxycarbonyl-(N-tert-butoxycarbonyl-L-phenylalanyl)$^3$-aglucoteicoplanin pentapeptide methyl ester [($N^B$-CBZ-(N-t-BOC-L-phenylalanyl)$^3$-ATPP methyl ester].

To a stirred solution of 1 g (about 0.9 mmol) of $N^B$-CBZ-ATTP methyl ester trifluoroacetate in 20 ml of dimethylformamide, 0.13 ml (about 0.9 mmol) of triethylamine is added at room temperature followed by 0.34 g (about 0.9 mmol) of the ester of N-t-BOC-L-phenylalanine with N-hydroxysuccinimide (Sigma Chemical Co., St. Louis, USA). After 3 hour stirring at room temperature, 100 ml of water is added and the resulting solution is adjusted at pH 3 with 1N HCl. Extraction with n-butanol (100 ml) and evaporation of the organic layer yield 0.9 g of $N^B$-CBZ-(N-t-BOC-L-phenylalanyl)$^3$-ATPP methyl ester (TABLE 2, compound 4; HPLC: Method B, $t_R$ 14.9 minutes);

ii) Preparation of [$N^B$-CBZ-(L-phenylalanyl)$^3$-ATPP methyl ester].

A solution of $N^B$-CBZ-(N-t-BOC-L-phenylalanyl)$^3$-ATPP methyl ester (220 mg) in 10 ml of dry trifluoroacetic acid is stirred at room temperature for 15 minutes and then the solvent is evaporated at 30° C. under reduced pressure. The oily residue is slurried with diethyl ether to give 200 mg N$^\beta$-CBZ-(L-phenylalanyl)$^3$-ATPP methyl ester as trifluoroacetate (TABLE 2, compound 5, analytical data reported for the free base; HPLC: Method B, t$_R$ 10.2 minutes).

EXAMPLE 3

Preparation of (L-phenylalanyl)$^3$-aglucoteicoplanin hexapeptide methyl ester [(L-phenylalanyl)$^3$-ATHP methyl ester; Reaction Scheme 1, formula (IV)].

i) Preparation of N$^\beta$-benzyloxycarbonyl-(L-phenylalanyl)$^3$-aglucoteicoplanin hexapeptide methyl ester [N$^\beta$-CBZ-(L-phenylalanyl)$^3$-ATHP methyl ester].

To a stirred solution of 0.4 g (about 0.34 mmol) of N$^\beta$-CBZ-(L-phenylalanyl)$^3$-ATPP methyl ester in 40 ml of a dimethylformamide: dichloromethane 1:1 mixture, 0.047 g (about 0.34 mmol) of N-hydroxybenzotriazole hydrate and 0.038 ml (about 0.34 mmol) of N-methylmorpholine are added at room temperature followed by 0.085 g (about 0.4 mmol) of dicyclohexylcarbodiimide. The reaction mixture is stirred at room temperature overnight and then the dichloromethane solvent is evaporated at 30° C. under reduced pressure. Afterwards, 200 ml of a water:ethyl acetate 1:1 mixture is added dropwise under stirring. The resulting mixture is adjusted at pH 3 with 1N HCl and the insoluble matter is filtered off. Then, the organic layer is separated and the solvent is evaporated at 35° C. under reduced pressure. The solid residue is dissolved in 50 ml of a mixture water:acetonitrile:n-butanol 1:1:2 and 5 g of silanized silica-gel 60 (0.06–0.2 mm; Merck) is added under stirring. After 30 minutes, the solvents are evaporated at 45° C. under reduced pressure and the solid residue is loaded on a column of 35 g of the same silanized silica-gel in water. The column is developed with a linear gradient from 10 to 70% of acetonitrile in water in 15 hours at the flow-rate of 100 ml/hour, while collecting 10 ml-fractions which are checked by HPLC. Those fractions containing pure title compound are pooled and an equal volume of n-butanol is added. The resulting solution is concentrated, at 40° C. under reduced pressure, to a small volume (about 10 ml), and then diethyl ether (100 ml is added). The precipitated solid is collected and added to 20 ml of dimethylsulfoxide. The resulting suspension is filtered and the clear filtrate is lyophilized, yielding 0.11 g of pure N$^\beta$-CBZ-(L-phenylalanyl)$^3$-ATHP methyl ester (TABLE 2, compound 6; HPLC: Method B, t$_R$ 22.6 minutes).

The $^1$H-NMR data (delta, ppm) of protons are reported hereinbelow (the protons identification is made in accordance with J. C. J. Barna, et al. J. Am. Chem. Soc. 1984, 106, 4895–4902): 8.69(w$_5$); 8.65(w$_7$); 8.38(w$_4$); 7.87(6b); 7.70 (w$_3$); 7.45(w$_2$); 6.60(w$_6$); 6.44(7d); 6.23(4b); 6.10(7f); 5.82 (x$_4$); 5.40(4f); 5.13(z$_6$); 4.97(CBZ—CH$_2$); 4.60(x$_2$); 4.60 (x$_5$); 4.54(x$_7$); 4.25(x$_3$); 4.24(x$_6$); 3.71(COO—CH$_3$); 2.85, 2.72(z$_2$,z$_2$'); 2.43, 2.25(Phe—CH$_2$).

ii) Preparation of (L-phenylalanyl)$^3$-ATHP methyl ester.

A solution of 1.8 g (about 1.5 mmol) of N$^\beta$-CBZ-(L-phenylalanyl)$^3$-ATHP methyl ester in 120 ml of a mixture methanol:1N HCl:dimethylformamide 6:2:1 is hydrogenated (1 atm, 25° C.) in the presence of 1.5 g of 5% Pd/C. The catalyst is filtered off and methanol is evaporated at 35° C. under reduced pressure; then, 100 ml of water is added and the resulting solution is extracted with 150 ml of ethyl acetate. The organic layer is discarded and the resulting aqueous suspension is extracted with 130 ml of n-butanol. The butanol phase is separated and concentrated at 30° C. under reduced pressure to a volume of about 20 ml. After addition of 150 ml of diethyl ether the precipitated solid is collected yielding 0.65 g of (L-phenylalanyl)$^3$-ATHP methyl ester as the hydrochloride (HPLC: Method B, t$_R$ 17.5 minutes, titer about 75%) which is used for the next step without any further purification.

EXAMPLE 4

Preparation of (L-phenylalanyl)$^3$-(D-lysyl)$^{15}$-aglucoteicoplanin dalbaheptide methyl ester [(L-phenylalanyl)$^3$-(D-lysyl)$^{15}$-ATDH methyl ester; Reaction Scheme 1, formula (Ic)]

i) Preparation of (L-phenylalanyl)$^3$-[N$^\alpha$,N$^\delta$-di-(tert-butoxycarbonyl)-D-lysyl] -aglucoteicoplanin dalbaheptide methyl ester [(L-phenylalanyl)$^3$-[N$^\alpha$,N$^\delta$-di-(t-BOC)-D-lysyl]$^{15}$-ATDH methyl ester)].

To a stirred solution of 0.29 g of crude (L-phenylalanyl)$^3$-ATHP methyl ester hydrochloride 3 ml of dimethylformamide, 0.07 ml triethylamine and 0.19 g of the ester of N$^\alpha$,N$^\delta$-di-(t-BOC)-D-lysine with N-hydroxy succinimide (prepared according to the method described by M. J. Marquisee and J. C. Kower, J. Med. Chem., 21: 1188–1194, 1978) are added at room temperature. After 1 day reaction, 50 ml of water is added and the resulting suspension is adjusted at pH 3 with 1N HCl; then, it is extracted with 50 ml of n-butanol. The organic layer is separated and washed with 25 ml of water; then, it is concentrated at 45° C. under reduced pressure to a small volume (about 3 ml). After addition of diethyl ether (30 ml), the precipitated solid is collected yielding 0.27 g of (L-phenylalanyl)$^3$-[N$^\alpha$,N$^\delta$-di-(t-BOC)-D-lysyl]$^{15}$-ATDH methyl ester, (HPLC: Method B, t$_R$ 22.5 minutes, titre about 45%). The compound is used without any purification for the final step.

ii) Preparation of (L-phenylalanyl)$^3$-(D-lysyl)$^{15}$-ATDH methyl ester.

The crude (L-phenylalanyl)$^3$-[N$^\alpha$,N$^\delta$-di-(t-BOC)-D-lysyl]$^{15}$-ATDH methyl ester (0.27 g) is dissolved at 10° C. in 5 ml of dry trifluoroacetic acid. After 10 minutes, the solvent is evaporated at 15° C. under reduced pressure. The oily residue is dissolved in 30 ml of a mixture water:methanol: 1:1 and the resulting solution is adjusted at pH 3.5 with 1N NaOH; then, it is loaded on a column of 50 g of silanized silica-gel. Column chromatography is performed as previously described for the purification of N$^\beta$-CBZ-(L-phenylalanyl)$^3$-ATHP methyl ester in EXAMPLE 3, obtaining 0.05 g of pure title compound as the trifluoroacetate. The product is then dissolved in 1 ml of water and the pH adjusted at 8.5 with 1N NaOH. The solid precipitate is collected and washed with water (2×2 ml), obtaining title compound (0.045 g) as the free base. (TABLE 2, compound 7; HPLC: Method B, t$_R$ 18.3 minutes).

The $^1$H-NMR data (delta ppm) of protons are reported hereinbelow (trifluoroacetate): 1.28, 1.45, 1.68, 2.93(Lys-CH$_2$s); 3.71(COO—CH$_3$); 4.14–5.34[peptidic alpha-CH's (x$_1$ to x$_7$; 4.14 ppm attributable to x$_1$, and 5.34 ppm to x$_4$]; 6.64–8.59(aromatic protons and peptidic NH's).

ANALYTICAL PROCEDURES

1) HPLC Methods

Reactions, column eluates and final products are checked by HPLC analyses, which are performed on a column LiChroCART (125×4 mm, Merck) pre-packed with LiChrospher RP (5 μm), using a Varian Model 5500 Liquid Chromatographic pump equipped with a 20 μl loop injector Rheodyne Model 7125 and a UV variable detector. Chromatograms are recorded at 254 nm. Elutions are carried out at a flow-rate of 1.5 ml/minutes by mixing Eluent (a): 0.2% aqueous ammonium formate, with Eluent (b): acetonitrile, according to linear step gradients programmed as follows:

Method A.

| Time (minutes): | 0 | 10 | 20 | 30 | 35 | 45 |
|---|---|---|---|---|---|---|
| % of (b) in (a): | 5 | 23 | 26 | 35 | 75 | 5 |

Method B:

| Time (minutes): | 0 | 30 | 35 | 40 | 45 |
|---|---|---|---|---|---|
| % of (b) in (a): | 20 | 60 | 75 | 75 | 20 |

2) Acid-base Titrations

Acid-base titrations are carried out under the following conditions: the sample is dissolved in a mixture methylcellosolve:water 4:1, then an excess of 0.01M HCl in the same solvent mixture is added and the resulting solution in titrated with 0.01N NaOH.

3) $^1$H NMR

The $^1$H NMR spectra are recorded in DMSO-$d_6$ solution at 303° K. on a Bruker AM 500 NMR-spectrometer equipped with an Aspect 3000 computer, using $(CH_3)_4$ Si (delta 0.00 ppm) as internal reference.

4) FAB-MS

FAB-MS positive ion spectra are obtained on a Kratos MS-50 double focusing mass spectrometer of 3000 dalton mass range, using 8 kV accelerating voltage. The instrument operates under computer control. To obtain high quality data, a DS-90 data-system in "raw data" acquisition is used. For FAB, a saddle field atom gun is used with Xe gas $(2\times10^{-5}$ torr pressure indicated on the source ion gauge) at 6 kV voltage and 1 mA current. The samples are dissolved in a mixture methanol:water 1:1 containing 0.2N HCl or, alternatively in dimethylformamide. Then, 1 microliter of this solution is mixed with 1 microliter of thioglycerol matrix, optionally containing 1N acetic acid on the target.

TABLE 2

Analytical Data

| Compound | Formula | M.W. | FAB-MS [M + H]$^+$ | Acid-base Titration E.W. |
|---|---|---|---|---|
| 1 | $C_{48}H_{45}N_5O_{16}Cl_2$ | 1018.8 | 1020 | 535 |
| 2 | $C_{56}H_{51}N_5O_{18}Cl_2$ | 1152.9 | 1154 | 1200 |
| 3 | $C_{51}H_{43}N_5O_{16}Cl_2$ | 1052.8 | 1054 | 573 |
| 4 | $C_{65}H_{60}N_6O_{19}Cl_2$ | 1300.1 | 1301 | 1285 |
| 5 | $C_{60}H_{52}N_6O_{17}Cl_2$ | 1200.0 | 1201 | 587 |
| 6 | $C_{60}H_{50}N_6O_{16}Cl_2$ | 1182.0 | 1183 | — |
| 7 | $C_{58}H_{56}N_8O_{15}Cl_2$ | 1176.0 | 1177 | 599 |

We claim:
1. An aglucodalbaheptide of general formula (I)

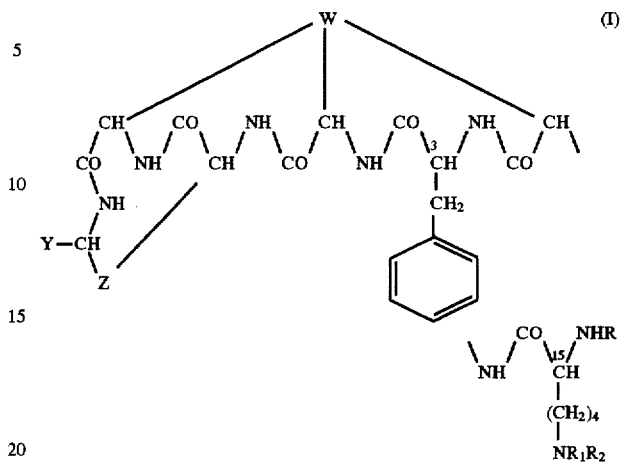

wherein:
W and Z, each independently, represent the relative portions of the aglycon of an antibiotic of the dalbaheptide group;
Y represents a carboxylic group or a functional derivative of said carboxylic group;
R and $R_1$, each independently, represent hydrogen or a protecting group of the amino function.
$R_2$ represents hydrogen;
and its salts with acid or bases as well as its inner salts.
2. An aglucodalbaheptide of claim 1 wherein Y, R, $R_1$ and $R_2$ are as in claim 1;
W is a group:

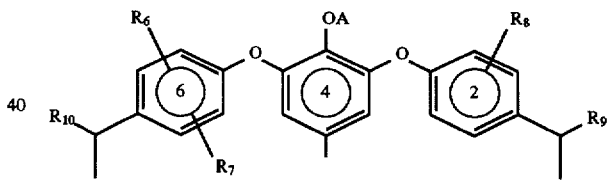

wherein:
A is hydrogen or a protecting group of the phenolic hydroxy moiety;
$R_6$, $R_7$ and $R_8$ are, each independently, hydrogen or halogen;
$R_9$ and $R_{10}$ are, each independently, hydrogen or a group $OR_{15}$ wherein $R_{15}$ is hydrogen or a protecting group of the benzylic hydroxy moiety;
Z is a group:

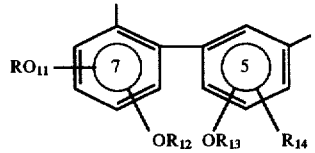

wherein:
the groups $OR_{11}$ and $OR_{12}$, are in, respectively, the para and ortho position with respect to the bond connecting the two phenyl rings and the radical $R_{11}$ and $R_{12}$, each independently, represent hydrogen or a protecting group of the phenolic hydroxy moiety; the group $OR_{13}$, preferably, is in the position ortho with respect to the bond connecting the two phenyl rings and the radical $R_{13}$ represents hydrogen or a protecting group of the phenolic hydroxy moiety; the group $R_{14}$, is in the position meta with respect to the bond connecting the two phenyl rings and represents hydrogen or halogen.

3. An aglucodalbaheptide of claim 1 of formula (Ia)

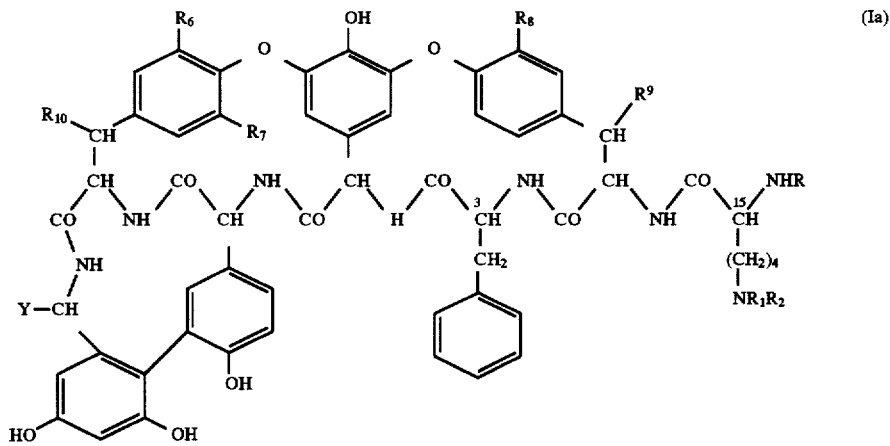

(Ia)

wherein:

Y represents a carboxylic group or a lower alkyl ester derivative of said carboxylic group;

R and $R_1$, each independently, represent hydrogen or a protecting group of the amino function;

$R_2$ represents hydrogen;

$R_6$ represents hydrogen;

$R_7$ and $R_8$, each independently, represent hydrogen or chloro;

$R_9$ represents hydrogen or hydroxy;

$R_{10}$ represents hydrogen or hydroxy;

and its salts with acids and bases.

4. An aglucodalbaheptide of claim 1 further characterized in that the absolute configuration of the chiral center identified with the index 3 is S and the absolute configuration of the chiral center identified with the index 15 is R or S.

5. An aglucodalbaheptide of claim 1 having the following formula

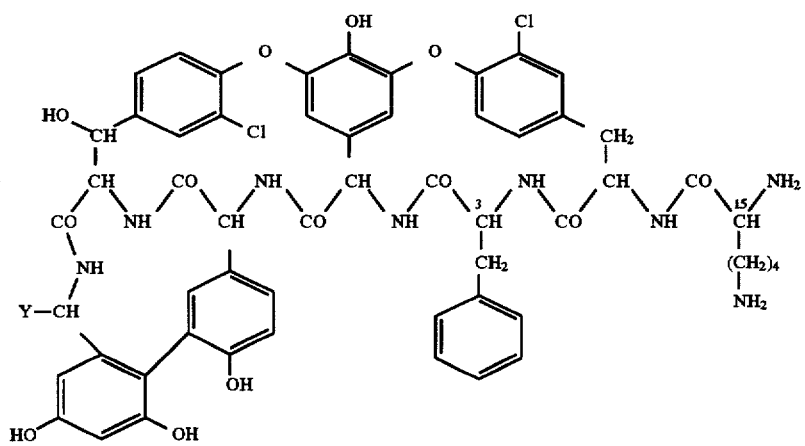

wherein

Y represents carboxy or carbomethoxy, and the chirality centers identified with the indexes 3 and 15 have, respectively, S and R absolute configuration;

and its pharmaceutically acceptable salts with acids and bases as well as its inner salts.

6. A process for the manufacture of an aglucodalbaheptide of the general formula (I)

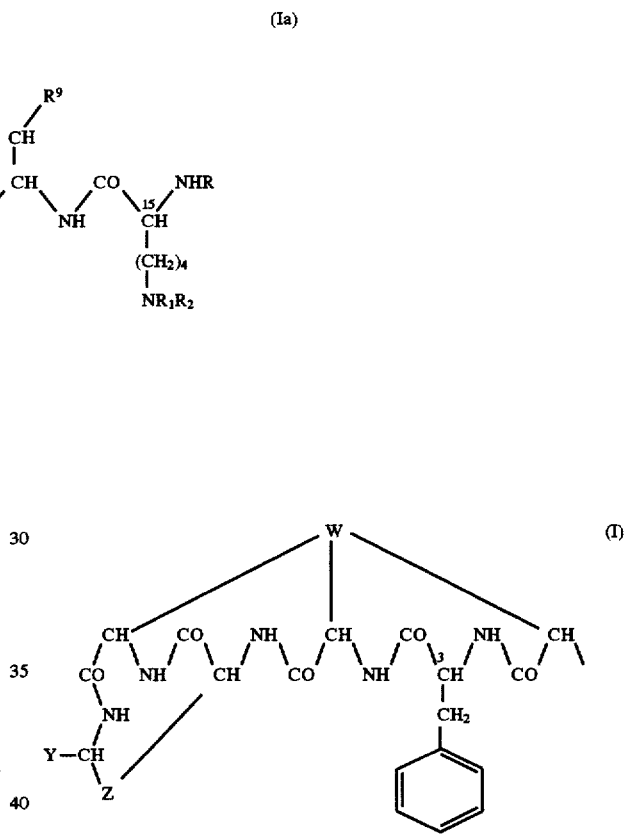

(I)

-continued

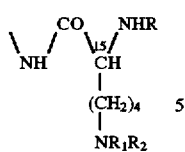

wherein:

W and Z, each independently, represent the relative portions of the aglycon of an antibiotic of the dalbaheptide group;

Y represents a carboxylic group or a functional derivative of said carboxylic group;

R and $R_1$, each independently, represent hydrogen or a protecting group of the amino function;

$R_2$ represents hydrogen;

and its salts with acid or bases as well as its inner salts, which comprises:

i) condensing a tetrapeptide of formula (IIb)

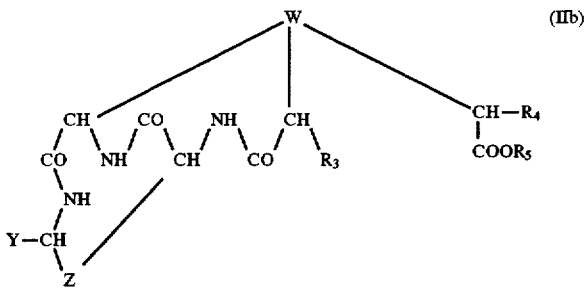

wherein:

W and Z have the same meanings as above;
Y is a functional derivative of the carboxylic group;
$R_3$ is amino;
$R_4$ is a protected amino group;
$R_5$ is hydrogen;

$R_5$ is hydrogen;

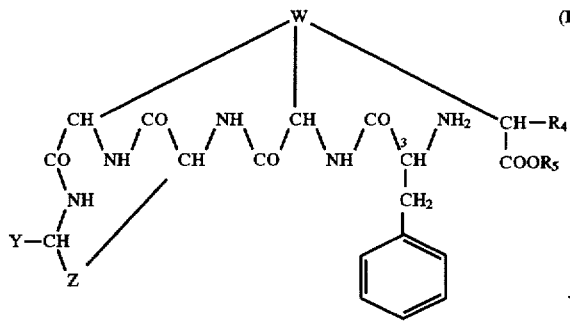

ii) submitting the pentapeptide of formula (III) to intramolecular condensation and successively deprotecting the protected amino group $R_4$ to yield an hexapeptide of formula (IV)

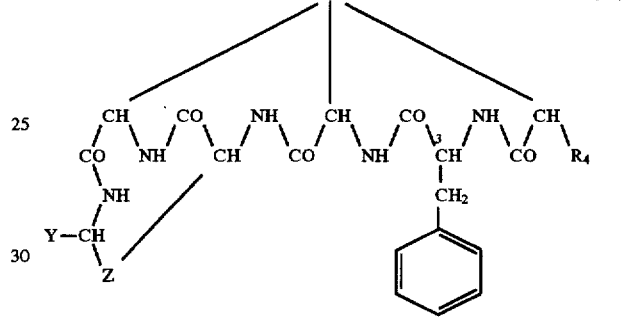

wherein:

W and Z have the same meanings as above;
Y is a functional derivative of the carboxylic group;
$R_4$ is amino;

iii) condensing the hexapeptide of formula (IV) with a $N^\alpha,N^\epsilon$-protected lysine derivative and, successively, deprotecting the amino groups of the lysine moiety yield the aglucodalbaheptide of formula (Ic)

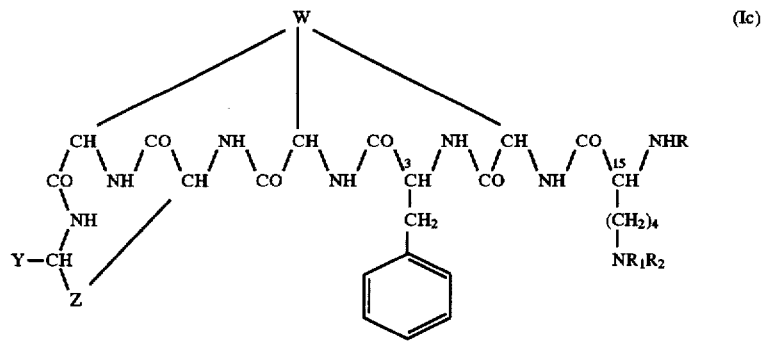

with a N-protected phenylalanine derivative and, successively, deprotecting the amino group of the phenylalanine moiety to yield a pentapeptide of formula (III)

wherein:

W and Z have the same meaning as above;

Y is a functional derivative of the carboxylic group;

$R_4$ is a protected amino group;

wherein:

W and Z have the same meaning as above;
Y is a functional derivative of the carboxylic group;
R is hydrogen;
$R_1$ is hydrogen;
$R_2$ is hydrogen;

iv) when Y is an easily cleavable protected carboxylic group, optionally deprotecting said protected carboxylic group of the compound of formula (Ic) to yield the corresponding carboxy derivative;

v) in case each of the portions W and Z of the compound of formula (Ic) contains protected phenolic or benzylic hydroxy groups, optionally removing said protecting groups;

vi) optionally transforming the free compound of formula (Ic) or its corresponding inner salts and its salts with acids and or bases.

7. A process as in claim 6 wherein in step i) the N-protected phenylalanine derivative is a L-phenyl-alanine derivative and in step iii) the $N^\alpha,N^\epsilon$-protected lysine derivative is a D-lysine derivative.

8. A process of claim 6 wherein the N-protecting group of the phenylalanine derivative is removable under conditions that do not affect the N-protecting group of the protected amino group $R_4$.

9. A process of claim 6, wherein the N-protecting group of the phenylalanine derivative is a tert-butoxycarbonylamino group and the N-protecting group of the protected amino group $R_4$ is a benzyloxycarbonylamino group.

10. A process of claim 6 wherein the N-protected phenylalanine derivative and $N^\alpha,N^\epsilon$-protected lysine derivative are activated on the carboxylic function with groups suitable for the formation of peptidic bonds.

11. A process as in claim 10 wherein the activating group of the carboxylic function is the ester formed between such carboxy group and N-hydroxysuccinimide.

12. An aglucodalbaheptide of claim 1 for use as a medicament.

13. A pharmaceutical composition containing an aglucodalbaheptide of claim 1 as the antibiotically active ingredient.

* * * * *